(12) United States Patent
Perbost et al.

(10) Patent No.: US 6,184,347 B1
(45) Date of Patent: Feb. 6, 2001

(54) MINIMIZATION OF BLOOMING IN HIGH-DENSITY ARRAYS BY USING REACTIVE WASH REAGENTS

(75) Inventors: Michel G. M. Perbost, Cupertino; Roy H. Kanemoto, Palo Alto, both of CA (US)

(73) Assignee: Agilent Technologies Inc., Palo Alto, CA (US)

( * ) Notice: Under 35 U.S.C. 154(b), the term of this patent shall be extended for 0 days.

(21) Appl. No.: 09/195,869

(22) Filed: Nov. 19, 1998

(51) Int. Cl.[7] .......................... A61K 38/04; C07H 21/00; G01N 15/06

(52) U.S. Cl. .......................... 530/333; 530/334; 536/25.3; 536/25.31; 422/50; 422/68.1

(58) Field of Search .................................. 530/333, 334; 536/25.3, 25.31; 422/50, 68.1

(56) References Cited

U.S. PATENT DOCUMENTS

| | | | |
|---|---|---|---|
| 4,417,046 | 11/1983 | Hsiung | 536/27 |
| 4,517,338 | 5/1985 | Urdea et al. | 525/54.11 |
| 4,849,513 | 7/1989 | Smith et al. | 536/27 |
| 4,980,460 | 12/1990 | Molko et al. | 536/23 |
| 5,015,733 | 5/1991 | Smith et al. | 536/23 |
| 5,026,838 | 6/1991 | Nojiri et al. | 536/27 |
| 5,039,796 | 8/1991 | Engels et al. | 536/27 |
| 5,047,524 | 9/1991 | Andrus et al. | 536/27 |
| 5,118,800 | 6/1992 | Smith et al. | 536/23 |
| 5,149,798 | 9/1992 | Agrawal et al. | 536/27 |
| 5,151,510 | 9/1992 | Stec et al. | 536/27 |
| 5,166,387 | 11/1992 | Hirschbein | 558/129 |
| 5,218,088 | 6/1993 | Gorenstein et al. | 536/25.34 |
| 5,268,464 | 12/1993 | Brill | 536/25.3 |
| 5,281,701 | 1/1994 | Vinayak | 536/25.34 |
| 5,292,875 | 3/1994 | Stec et al. | 536/25.33 |
| 5,310,894 | 5/1994 | Zeiger | 536/25.3 |
| 5,324,831 | 6/1994 | Marquez et al. | 536/25.3 |
| 5,420,330 | 5/1995 | Brush | 558/185 |
| 5,436,143 | 7/1995 | Hyman | 435/91.2 |
| 5,436,327 | 7/1995 | Southern et al. | 536/25.34 |
| 5,446,137 | 8/1995 | Maag et al. | 536/23.1 |
| 5,451,463 | 9/1995 | Nelson et al. | 428/402 |
| 5,464,759 | 11/1995 | Coolidge et al. | 435/91.2 |
| 5,512,667 | 4/1996 | Reed et al. | 536/24.31 |
| 5,512,668 | 4/1996 | Stec et al. | 536/25.33 |
| 5,574,146 | 11/1996 | Reddy et al. | 536/25.34 |
| 5,623,068 | 4/1997 | Reddy et al. | 536/25.34 |
| 5,625,052 | 4/1997 | Woo et al. | 536/25.34 |
| 5,679,785 | 10/1997 | Engels et al. | 536/25.32 |
| 5,688,940 | 11/1997 | Lyttle | 536/25.3 |
| 5,695,979 | 12/1997 | Caruthers et al. | 435/184 |
| 5,700,919 | 12/1997 | Seliger et al. | 536/22.1 |
| 5,705,621 | 1/1998 | Ravikumar | 536/23.1 |
| 5,714,597 | 2/1998 | Ravikumar et al. | 536/25.31 |
| 5,716,784 | 2/1998 | Di Cesare | 435/6 |
| 5,723,599 | 3/1998 | Klem et al. | 536/25.3 |
| 5,734,041 | 3/1998 | Just et al. | 536/25.31 |
| 5,741,900 | 4/1998 | Gmeiner et al. | 536/25.31 |

(List continued on next page.)

FOREIGN PATENT DOCUMENTS 0 563 010 A2   9/1993   (EP) .

Primary Examiner—Ardin H. Marschel

(57) ABSTRACT

A wash reagent employed for the bulk washing of the surface of a high-density array to remove unreacted reactants from cells of the array while, at the same time, reacting with the unreacted monomer in order to prevent reaction of the reacted monomer with functional groups on the surface of the HDA outside of the region of the surface to which the reactive monomer is applied. The wash reagent is chosen for a particular solid-state synthesis so that the unreacted reactants and catalyzing agents are soluble in the wash reagent, so that the wash reagent does not react with, or catalyze, reactions of the substrate or the biopolymers bound to the substrate, and so that the wash reagent reacts with unreacted reactive monomer in order to prevent subsequent reactions of the unreacted reactive monomer.

15 Claims, 9 Drawing Sheets

U.S. PATENT DOCUMENTS

| | | | |
|---|---|---|---|
| 5,763,594 | 6/1998 | Hiatt et al. | 536/25.3 |
| 5,783,684 | 7/1998 | Reddy et al. | 536/25.3 |
| 5,789,576 | 8/1998 | Daily et al. | 536/25.6 |
| 5,807,522 * | 9/1998 | Brown et al. | 422/50 |

* cited by examiner

5'- Dimethoxytrityl-N-benzoyl-2'-deoxyAdenosine,3'-[(O-cyanoethyl)-(N,N-diisopropyl)]-phosphoramidite

MINIMIZATION OF BLOOMING IN HIGH-DENSITY ARRAYS BY USING REACTIVE WASH REAGENTS

TECHNICAL FIELD

The present invention relates to the preparation of high-density arrays of surface-bound oligonucleotides by a stepwise synthesis of oligonucleotides on the surface of a substrate and, in particular, to a method and system for precisely confining the application of reactive deoxynucleoside phosphoramidites to particular cells within the high-density array.

BACKGROUND OF THE INVENTION

A combination of synthetic chemical technologies and certain computer-related technologies has lead to the development of an important analytical tool in the field of molecular biology commonly referred to as the "gene chip." Gene chips are high-density arrays of oligonucleotides bound to a chemically prepared substrate such as silicon, glass, or plastic. Each cell, or element, within the array is prepared to contain a single oligonucleotide species, and the oligonucleotide species in a given cell may differ from the oligonucleotide species in the remaining cells of the high-density array. Gene chips may be used in DNA hybridization experiments in which radioactively, fluorescently, or chemiluminescently labeled DNA or RNA molecules are applied to the surface of the gene chip and are bound, via Watson-Crick base pair interactions, to specific oligonucleotides bound to the gene chip. The gene chip can then be analyzed by radiometric or optical methods to determine to which specific cells of the gene chip the labeled DNA or RNA molecules are bound. Thus, in a single experiment, a DNA or RNA molecule can be screened for binding to tens or hundreds of thousands of different oligonucleotides.

Hybridization experiments can be used to identify particular gene transcripts in mRNA preparations, to identify the presence of genes or regulatory sequences in cDNA preparations, or to sequence DNA and RNA molecules. Particularly in the latter application, the effectiveness of employing gene chips depends of the precision with which specific oligonucleotides can be synthesized within discrete cells of the gene chip. As with any chemical synthetic process, various factors may cause the yields of specific steps in the synthesis of oligonucleotides to be less than 100%, leading to unintended and unwanted intermediate species. During an oligonucleotide lengthening step in the synthesis of oligonucleotides on the surface of a gene chip, reactive deoxynucleoside phosphoramidites are successively applied, in concentrations exceeding the concentrations of target hydroxyl groups of the substrate or growing oligonucleotide polymers, to specific cells of the high-density array. Then, unreacted deoxynucleoside phosphoramidites from multiple cells of the high-density array are washed away in a single wash step to prepare for a subsequent step of oligonucleotide synthesis. Unfortunately, during the wash step, unreacted deoxynucleoside phosphoramidites may migrate to regions outside the specific region of the high-density array to which they were applied and react with functional groups of the high-density array substrate or bound oligonucleotides rather than being cleanly removed from the surface of the gene chip. These unintended deoxynucleoside phosphoramidite reactions may result in the spreading, or blooming, of the deoxynucleoside phosphoramidite reaction to adjoining regions of the gene chip and may even lead to cross contamination of adjoining cells. As a consequence, the cells of the high-density array may end up containing a mixture of different oligonucleotides rather than a single specific oligonucleotide. A related blooming problem may occur when various phosphoramidite dyes are applied to the surface of the gene chip to mark specific cells or features. Blooming of these phosphoramidite dyes may lead to imprecise and low-resolution marking of cells and features.

Although a method for successively removing unreacted phosphoramidite reactants from individual cells of the high-density array might be envisioned, such successive treatment of individual cells would greatly increase the time required for preparation of gene chips, and would increase the complexity of the mechanical devices that are used to prepare gene chips. Instead, a need has been recognized in the area of gene chip manufacture for a method for bulk removal of unreacted phosphoramidite reactants from the cells of a high-density array without producing the blooming phenomenon resulting from reactions of phosphoramidite reactants outside the specific areas of a gene chip to which they are originally applied.

SUMMARY OF THE INVENTION

The present invention provides a method for the bulk removal of unreacted phosphoramidite reactants from the surface of a high-density array so that the unreacted phosphoramidite reactants do not react with reactive functional groups of the substrate of the high-density array or with chemical species bound to the substrate of the high-density array in areas outside of the specific area to which the phosphoramidite reactants are originally applied. In the method of the present invention, a phosphoramidite-reactive solution is employed to wash unreacted phosphoramidites from the surface of the high-density array. The phosphoramidite-reactive solution reacts with, and deactivates, unreacted phosphoramidites before they have a chance to react with reactive functional groups of either the substrate of the high-density array or of chemical species bound to the substrate of the high-density array. Use of the present invention thus allows for the preparation of high-density arrays with densities, or resolutions, determined by the precision with which the phosphoramidite reactants can be applied to the surface of the high-density array.

DETAILED DESCRIPTION OF THE INVENTION

Figure 1A:
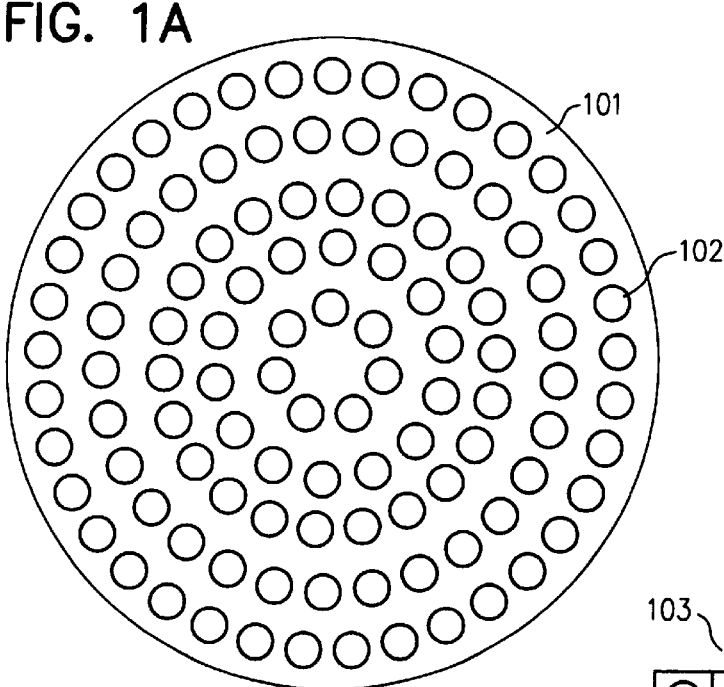
FIGS. 1A–1D illustrate small regions of two different types of high-density arrays containing substrate-bound oligonucleotides.
Figure 1B:

FIGS. 1A–1D illustrate two small regions of two different types of high-density arrays ("HDAs") containing surface-bound oligonucleotides. The first type of HDA, shown in FIGS. 1A–1B, has disk-shaped surface regions, or cells, that each contain a particular synthesized biopolymer like, for example, cell 102. FIG. 1A shows a number of cells of small disk-shaped region of an HDA viewed in a direction orthogonal to the surface of the HDA, and FIG. 1B shows a cross-section of the region of the HDA shown in FIG. 1A. The cells are laid out on the surface of the HDA along concentric circles, as shown in FIG. 1A, or in a matrix or grid-like arrangement (not shown). Each cell has a precisely defined location on the surface of the HDA that can be located by analytical devices that analyze labeled molecules bound to the surface of a cell using radiometric or optical methods. Biopolymers may be synthesized on the surface of the HDA in a step-wise fashion so that each cell of the HDA may contain a different biopolymer. Solutions containing the necessary reactants for synthesizing substrate-bound biopolymers are applied in small droplets to the cells and spread by surface tension and adsorption to the hydrophilic substrate, into a disk-shaped region of increasing radius. The inter-cell regions of the HDA surface are treated with a reagent that chemically modifies the surface of the HDA to prevent reactive monomers from covalently bonding to the inter-cell surface of the HDA during biopolymer synthesis.

Figure 1C:
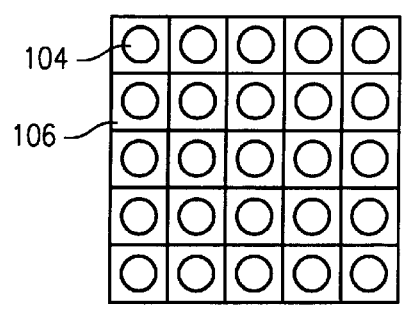
Figure 1D:
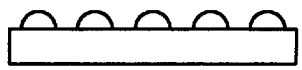

FIG. 1C shows 25 cells of a square region of a second type of HDA containing surface-bound oligonucleotides viewed in a direction orthogonal to the surface of the HDA. FIG. 1D shows a cross-section of the region of the HDA shown in FIG. 1C. The cells of this type of HDA form a regular grid, or matrix, as shown in FIG. 1C, or are laid out along concentric circles like the HDA shown in FIG. 1A. The reactants required during the synthetic steps are added to tiny surface tension wells, for example, surface tension well 104. These surface tension wells lie above circular regions of the substrate of the HDA that are chemically prepared to provide reactive groups to which the first monomer of a growing biopolymer can be chemically bound. Intervening regions of the HDA surface 106 outside the perimeter of the surface tension wells may be chemically prepared to present a hydrophobic surface that causes aqueous solutions added to the surface tension wells to bead up into semi-spherical droplets and to remain constrained within the circular area of the HDA cell to which the aqueous solutions are applied.

In one method for preparing HDAs, a device similar to the ink jet printers used for the computer-controlled printing of text and diagrams onto paper is used to successively deposit tiny droplets, each containing one or more specific reactants, to cells of an HDA during each synthetic step of the synthesis of substrate-bound biopolymers. Using inkjet technology, an HDA may be prepared to contain 100,000 disk-shaped cells or semi-spherical surface tension wells, each having a diameter of approximately 100 microns, on the surface of a circular region of an HDA having a diameter of 75 mm. Each cell or surface tension well may have a volume on the order of 100 pl.

The present invention will be described in terms of a preferred embodiment related to HDAs of the type shown in FIGS. 1A–1B containing oligonucleotides prepared by stepwise addition of reactive deoxynucleoside phosphoramidites to the cells. However, one skilled in the art of the preparation of HDAs will appreciate that the present invention may find application in the preparation of different types of HDAs, like, for example, the type of HDA shown in FIGS. 1C–1D, and in the preparation of HDAs containing other types of biopolymers prepared by step-wise polymerization of different types of reactive monomers.

Figure 2:
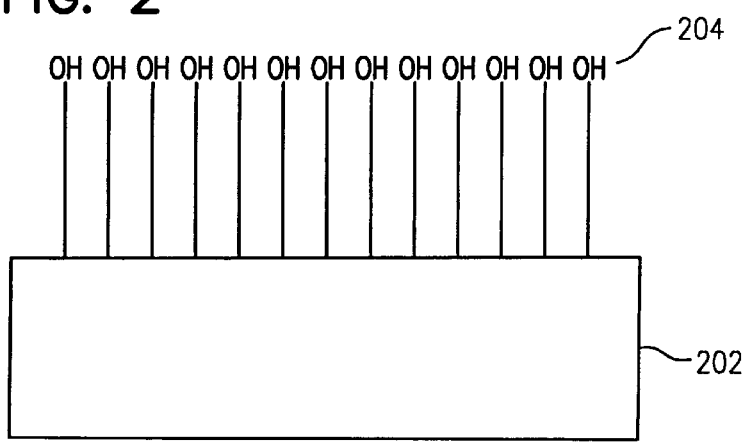
FIG. 2 illustrates, in cross-section, the surface of a high-density array prior to the synthesis of surface-bound biopolymers.

FIG. 2 illustrates, in cross-section, the surface of an HDA within a cell prior to the synthesis of the biopolymers that will be bound to the surface of the HDA. The substrate of the HDA 202 is prepared to present reactive functional groups, in the present case, hydroxyl groups 204, at the surface that will serve as anchors to which synthesized biopolymers will be bound.

Figure 3:
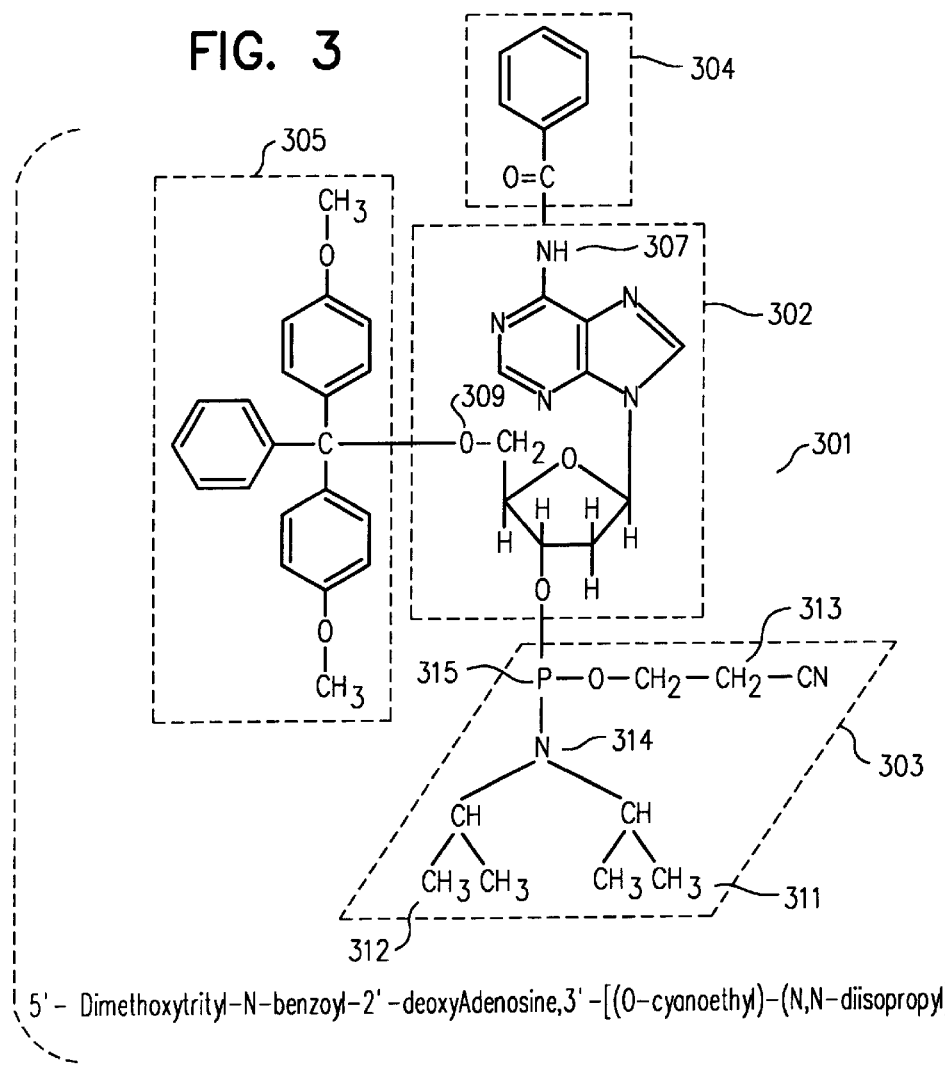
FIG. 3 illustrates the deoxynucleoside phosphoramidite 5'-Dimethoxytrityl-N-benzoyl-2'deoxyAdenosine,3'-[(O-cyanoethyl)-(N,N-diisopropyl)]-phosphoramidite.

Deoxynucleoside phosphoramidites are used as reactive monomers for the step-wise synthesis of oligonucleotides. FIG. 3 illustrates the deoxynucleoside phosphoramidite 5'-Dimethoxytrityl-N-benzoyl-2'-deoxyAdenosine,3'-[(O-cyanoethyl)-(N,N-diisopropyl)]-phosphoramidite. This monomer is composed of four different subcomponent groups 302–305, enclosed in FIG. 3 within dashed lines. The first subcomponent group 302 is a deoxynucleoside. In FIG. 3, the deoxynucleoside illustrated is adenosine. Other deoxynucleoside phosphoramidites used in the synthesis of oligonucleotides contain guanosine, cytidine, and thymidine in place of the adenosine 302 shown in FIG. 3. A benzoyl group 304 is linked through an amide bond to $N^6$ of the adenosine group 302. This benzoyl group protects the primary amine of the adenosine group from reacting with the phosphoramidite group of a second deoxynucleoside phosphoramidite. The primary amines of guanosine and cytidine are similarly protected in the other deoxynucleoside phosphoramidites. Different types of protecting groups are available, including, for example, acetyl or isobutyryl groups. A dimethoxytrityl ("DMTr") group 305 is linked to the 5' end of the deoxynucleoside group in order to protect the 5' hydroxyl group of the deoxynucleoside from reacting with the phosphoramidite group of another deoxyphosphoramidite. Finally, a phosphoramidite group 303 is linked to the 3' end of the adenosine group 302. A variety of different phosphoramidite groups may be employed in which different types of alkyl groups may be substituted for the isopropyl groups 311–312 linked to the amine nitrogen atom 314 of the phosphoramidite group 303 and the cyanoethyl group 313 linked via a phosphite ester bond to the phosphorous atom 315 of the phosphoramidite group 303.

Figure 4:
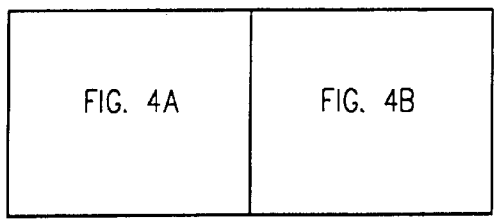

FIG. 4 illustrates the chemical steps employed to link the first protected deoxynucleoside phosphoramidite monomer to a free hydroxyl group on the surface of the HDA. A solution containing a protected deoxynucleoside phosphoramidite 402 and tetrazole, S-ethyl tetrazole, or dicyanoimidazole is applied to the surface of the HDA that has been chemically prepared to present free hydroxyl groups 406. Tetrazole, S-ethyl tetrazole, and dicyanoimidazole are acids that protonate the amine nitrogen 404 of the phosphoramidite group of the deoxynucleoside phosphoramidite 402. A free hydroxyl group 406 on the surface of the substrate displaces the protonated secondary amine group of the phosphoramidite group by nucleophilic substitution and results in the protected deoxynucleoside covalently bound to the substrate via a phosphite triester group 408. After a wash step, in which unreacted deoxynucleoside phosphoramidites and tetrazole, S-ethyl tetrazole, or dicyanoimidazole are removed, free hydroxyl groups of the substrate of the HAD, particularly free hydroxyl groups of the inter-cell regions of the substrate of the HAD 410, are acetylated 412 by application of a solution of CAP A, comprising acetic anhydride, 2,6-lutidine (2,6-dimethylpyridine), and terahydrofuran ("THF"); and CAP B, comprising 1-methyl-imidazole in THF. After a wash step, in which the CAP A/CAP B solution is removed, the phosphite triester group is oxidized by the addition of iodine in THF, 2,6-lutidine, and water to form a phosphotriester group 414.

Figure 5:
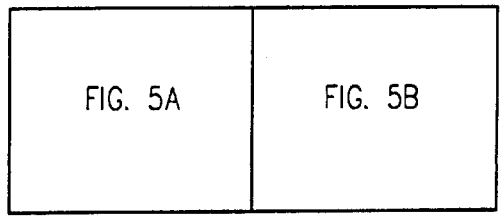

FIG. 5 illustrates the addition of a deoxyphosphoramidite monomer to a growing oligonucleotide polymer attached to the surface of the HDA. After any unreacted reagents from previous synthetic steps are removed by washing, the DMTr protecting group of the 5' terminal nucleosides of the growing oligonucleotides are removed by treatment with acid to produce a free 5'-hydroxyl group 502–503. Next, a protected deoxynucleoside phosphoramidite (DMTr-N-benzoyl-deoxyCytidine phosphoramidite in FIG. 5) in solution with tetrazole is applied to the substrate-bound oligonucleotide and reacts with the 5' hydroxyl of the oligonucleotide to covalently link the protected deoxynucleoside 504 to the 5' end of the oligonucleotide via a phosphite triester group 506. After excess, unreacted protected deoxynucleoside phosphoramidites and tetrazole are removed by washing, any unreacted 5' hydroxyl groups 508 of substrate-bound oligonucleotides are acetylated 510 by application of a CAP A/CAP B solution. This step is necessary because the previous oligonucleotide elongation reaction does not proceed to 100% completion, and it is desirable to terminate any unreacted nucleotides by acetylation so that oligonucleotides with incorrect sequences are not produced in subsequent synthetic steps. After the CAP A/CAP B solution is removed by washing with acetonitrile, the phosphite triester group 512 is oxidized to a phosphotriester group 514 by the addition of $I_2$, THF, 2,6-lutidine, and $H_2O$. The steps illustrated in FIG. 5 are repeated to add each additional deoxynucleoside to the 5' end of the growing oligonucleotide.

A particular deoxynucleoside phosphoramidite reactant can be added to each cell of the HDA during each synthetic cycle. Thus, for example, protected deoxyadenosine phosphoramidite may be added to one cell and protected deoxyguanosine phosphoramidite may be added to an adjoining cell during the first synthetic cycle. Thus, the oligonucleotide species synthesized in the first cell will have adenylic acid at the 3' terminus and the oligonucleotide species synthesized in the adjoining cell will have guanylic acid at the 3' terminus. At the completion of the synthetic cycles, each cell of the HDA may contain an oligonucleotide species having a nucleotide sequence different from the nucleotide sequences of all the other oligonucleotides synthesized in the other cells of the HDA.

Figure 6:
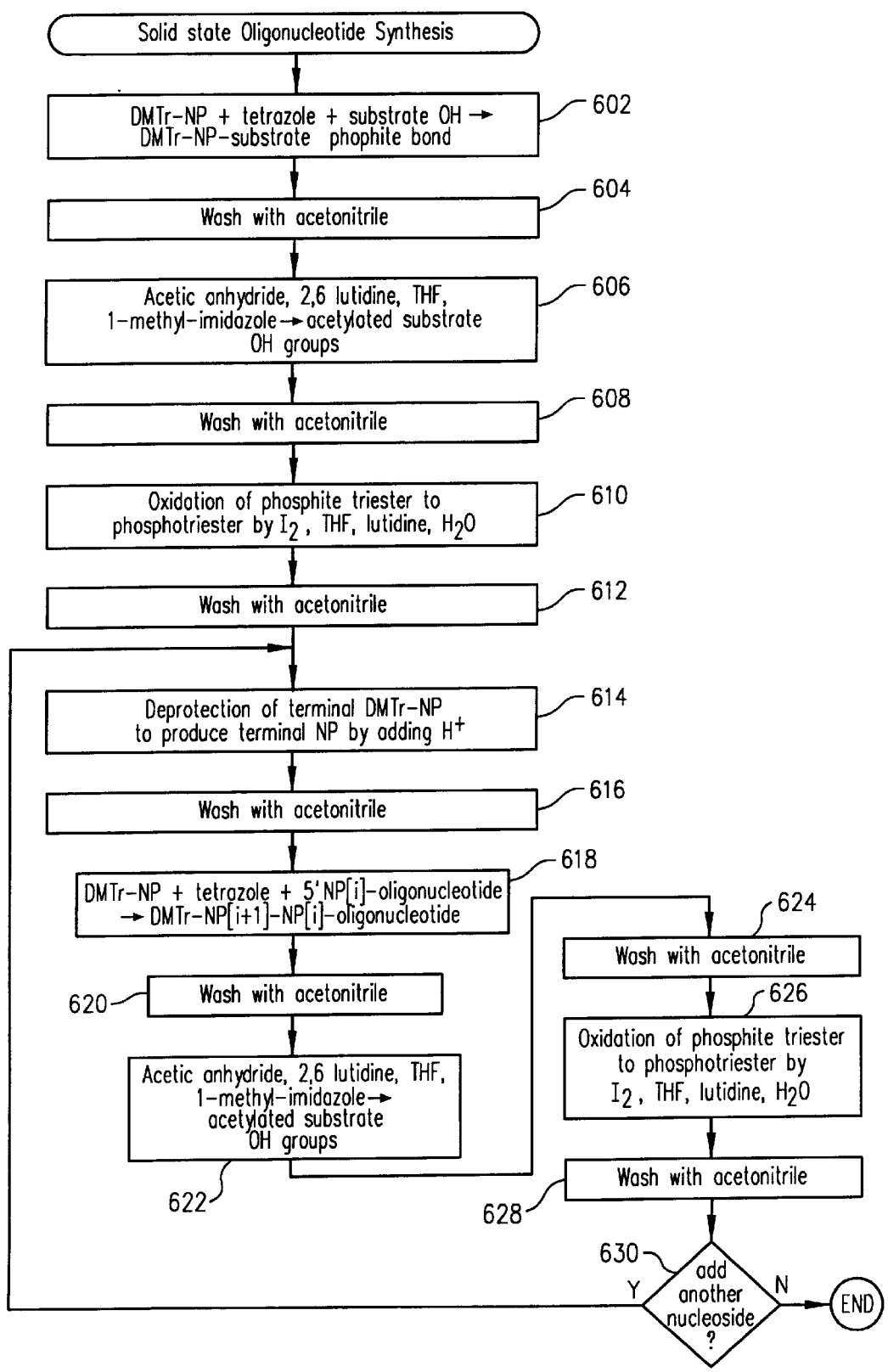
FIG. 6 is a flow diagram that shows the sequence of steps employed to synthesize substrate-bound oligonucleotides on the surface of a high-density array.

FIG. 6 is a flow diagram that shows the sequence of steps employed to synthesize substrate-bound oligonucleotides on the surface of an HDA. These steps are illustrated in FIGS. 4 and 5. In the first step 602, a protected deoxynucleoside phosphoramidite is applied, along with tetrazole, S-ethyl tetrazole, or dicyanoimidazole, to those cells of the HDA in which the synthesis of oligonucleotides will be initiated. Although represented in FIG. 6 as a single step, this step is actually composed of many thousands of successive applications of protected deoxynucleoside phosphoramidites to individual cells of the HDA. In step 604, unreacted deoxynucleoside phosphoramidites and tetrazole, S-ethyl tetrazole, or dicyanoimidazole are removed from the surface of the HDA by washing, in a single step, the surface of the HDA with a solvent. Currently, the solvent acetonitrile is employed as the wash reagent. In step 606, unreated substrate hydroxyl groups are acetylated by application of a CAP A/CAP B solution. In step 608, the CAP A/CAP B solution is removed by washing with acetonitrile. In step 610, the phosphite triester group linking the newly added protected deoxynucleoside is oxidized, by the addition of $I_2$, THF, 2,6-lutidine, and $H_2O$, to form a phosphotriester group. In step 612, the oxidizing solution is removed by washing the surface of the HDA with the wash reagent acetonitrile. In step 614, the protecting dimethoxytrityl group on the 5' end of the growing oligonucleotide within designated cells of the HDA is removed by the addition of acid. In step 616, the added acid and freed dimethoxytrityl groups are removed from the surface of the HDA by washing the surface of the HDA with the wash reagent acetonitrile. In step 618, the next protected deoxynucleosides to be added to the oligonucleotides in the designated cells are applied to the designated cells along with tetrazole, S-ethyl tetrazole, or dicyanoimidazole in many thousands of successive applications. The applied protected deoxynucleoside phosphoramidite reacts with the 5' hydroxyl group at the 5' terminus of the growing oligonucleotide and is thereby covalently linked to the growing oligonucleotide through a phosphite triester group. In step 620, unreacted protected deoxynucleoside phosphoramidites and tetrazole, S-ethyl tetrazole, or dicyanoimidazole are removed from the surface of the HDA by washing, in a single step, the surface of the HDA with the wash reagent acetonitrile. In step 622, unreacted 5'-hydroxyl groups are acetylated by application of a CAP A/CAP B solution. In step 624, the CAP A/CAP B solution is removed by washing with acetonitrile. In step 626, the phosphite triester group is oxidized by the addition of $I_2$, THF, 2,6-lutidine, and $H_2O$ to form a phosphotriester group. In step 628, the oxidizing solution is removed from the surface of the HDA by washing the surface of the HDA with the wash reagent acetonitrile. If another nucleoside is to be added to the growing oligonucleotides in any of the cells of the HDA, as detected in step 630, steps 614–628 are repeated, starting at step 614. Otherwise, oligonucleotide synthesis is complete.

Figure 7:
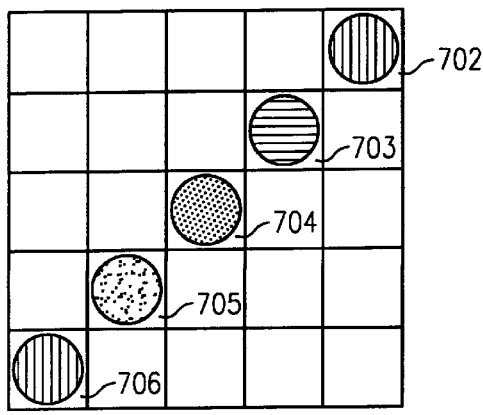
FIG. 7 illustrates the application of four different deoxynucleoside phosphoramidites to five cells of a 25-cell region on the surface of a high-density array.

FIG. 7 illustrates the application of four different deoxynucleoside phosphoramidites to five cells of a 25-cell grid-like region on the surface of an HDA. The different protected deoxynucleoside phosphoramidite and tetrazole solutions have been applied, in successive applications, to the five cells 702–706 along the diagonal of the 25-cell region. In one method of HDA preparation, a device incorporating high-speed ink jet technology successively locates those cells on an HDA that are designated to receive a protected deoxynucleoside phosphoramidite during the next synthetic cycle and applies tiny droplets, on the order of 100 pl, of the designated one of the four different types of protected deoxynucleoside phosphoramidites to the designated cells. Such devices can seek and apply the designated deoxynucleoside phosphoramidite to several hundred cells per second. Thus, the appropriate protected deoxynucleoside phosphoramidite may be applied to each cell of a 100,000-cell HDA in the course of a single synthetic step within a period of between 5 and 10 minutes. After the protected deoxynucleoside phosphoramidite solutions have been applied to each of cells 702–706, the protected deoxynucleoside phosphoramidites will react with, and become covalently bound through phosphite triester groups to, any free reactive functional groups of the substrate or growing bound oligonucleotides. Because the protected deoxynucleoside phosphoramidites are applied in quantitative excess, the cells 702–706 will contain unreacted protected deoxynucleoside phosphoramidites.

Figure 8:
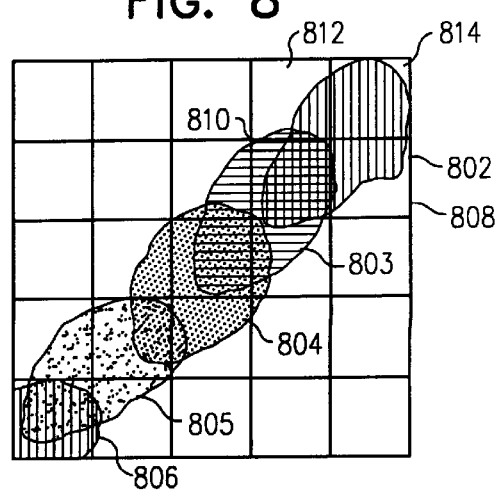
FIG. 8 shows the spreading, or blooming, of deoxynucleoside phosphoramidites on the surface of a high-density array.
Figure 4A:
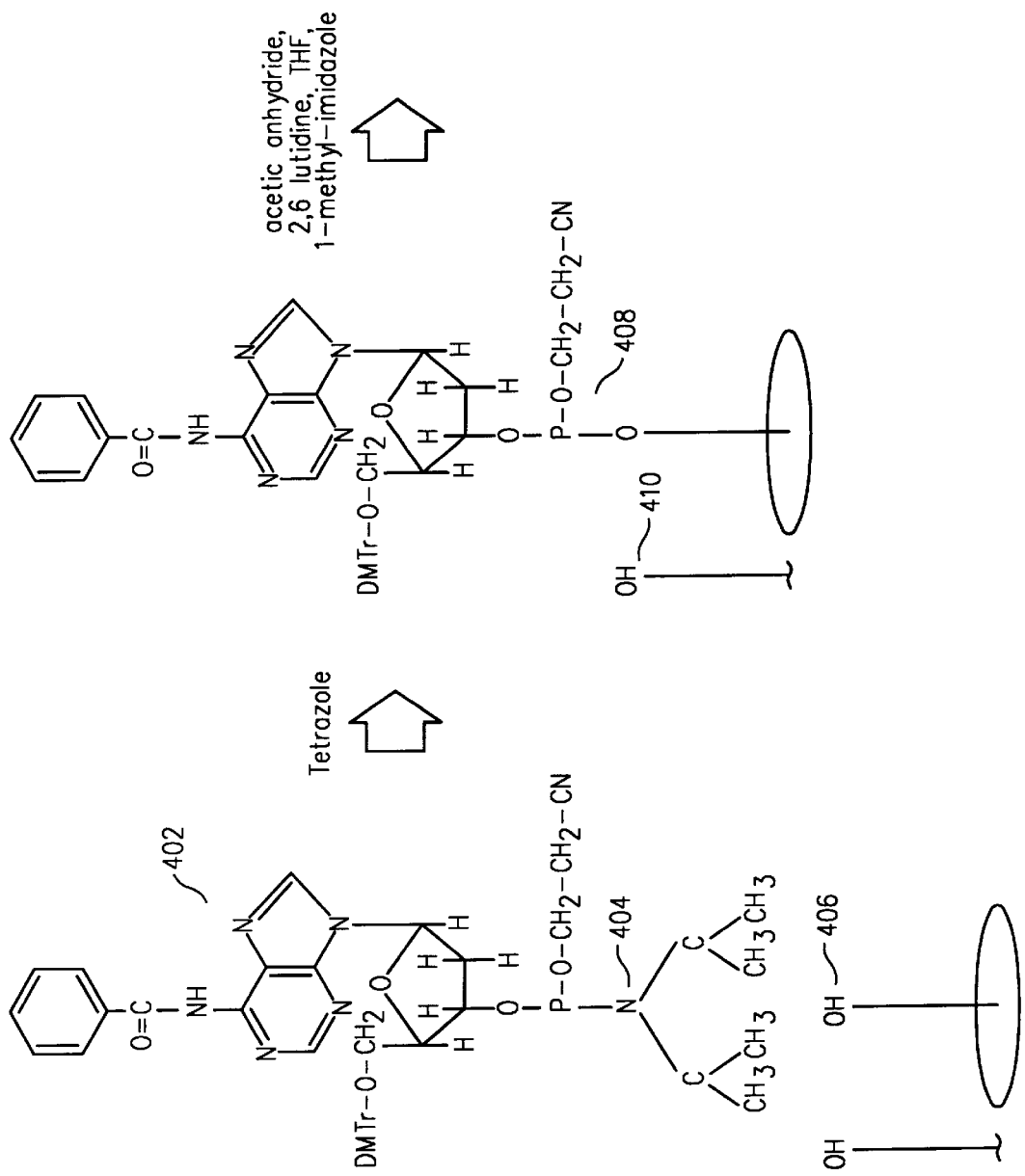
FIG. 4 illustrates the chemical steps employed to link a first deoxynucleoside phosphoramidite monomer to a free hydroxyl group on the surface of a high-density array.
Figure 4B:
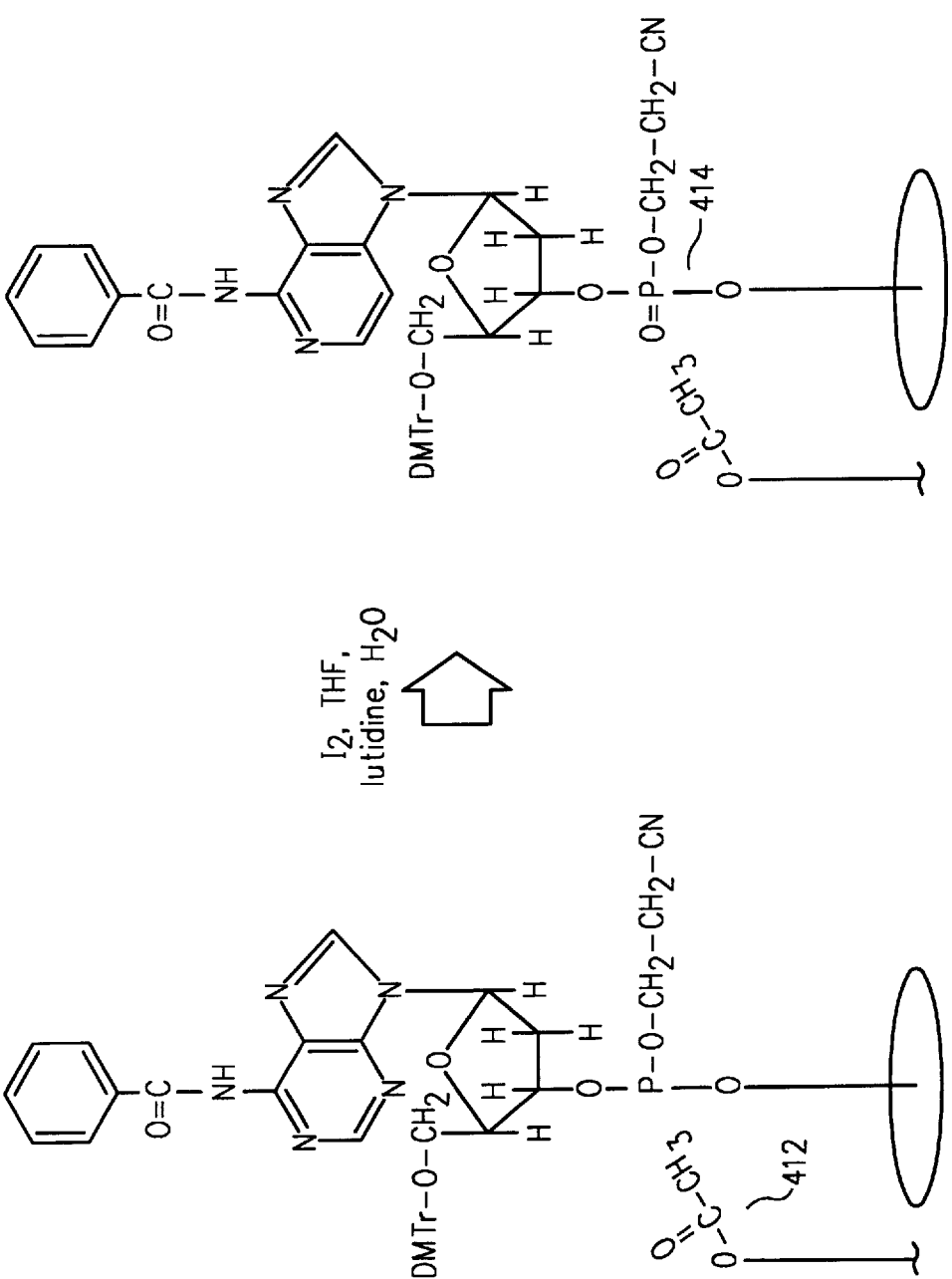
Figure 5A:
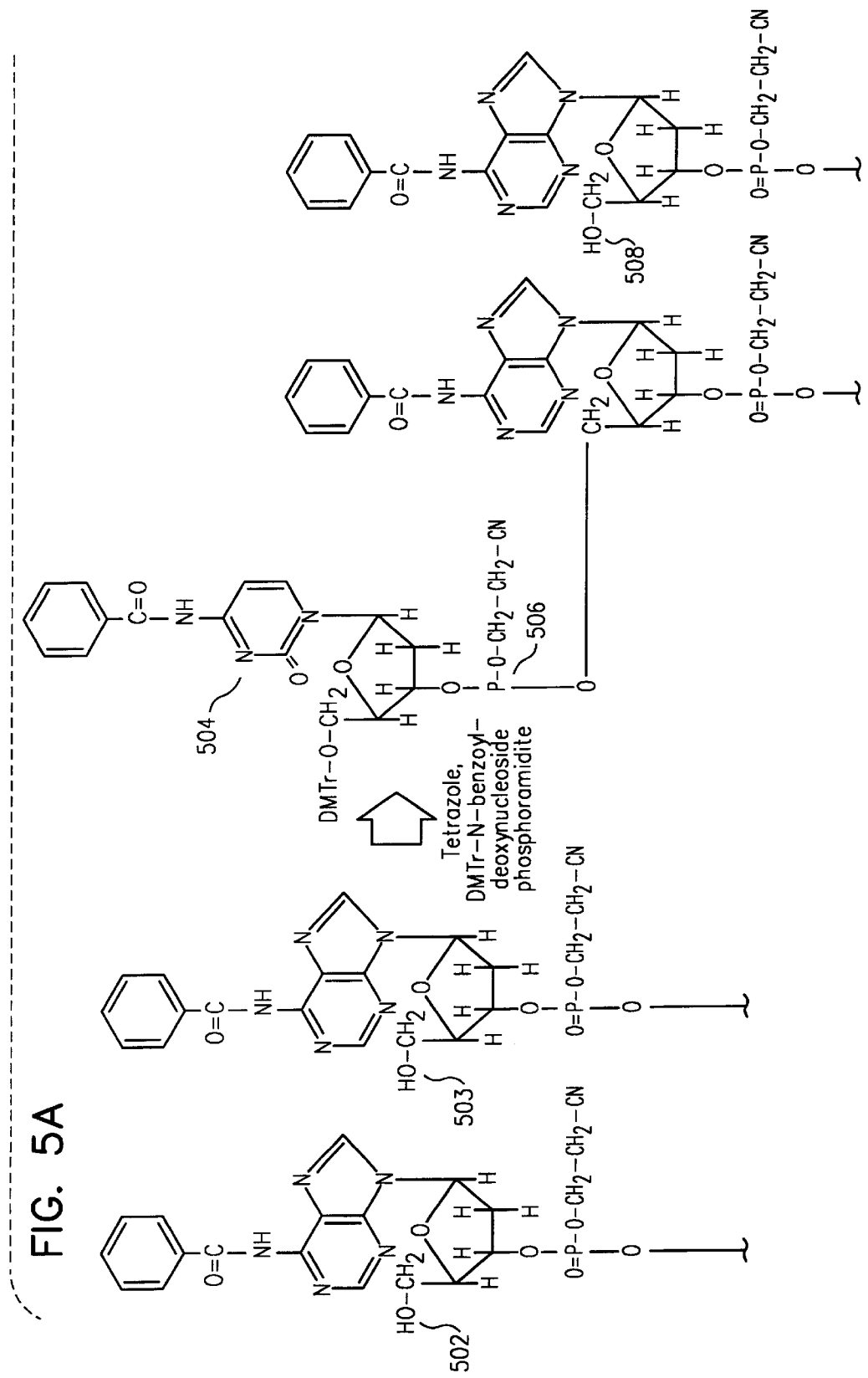
FIG. 5 illustrates the addition of a deoxynucleoside phosphoramidite monomer to a growing oligonucleotide polymer bound to the surface of a high-density array.
Figure 5B:
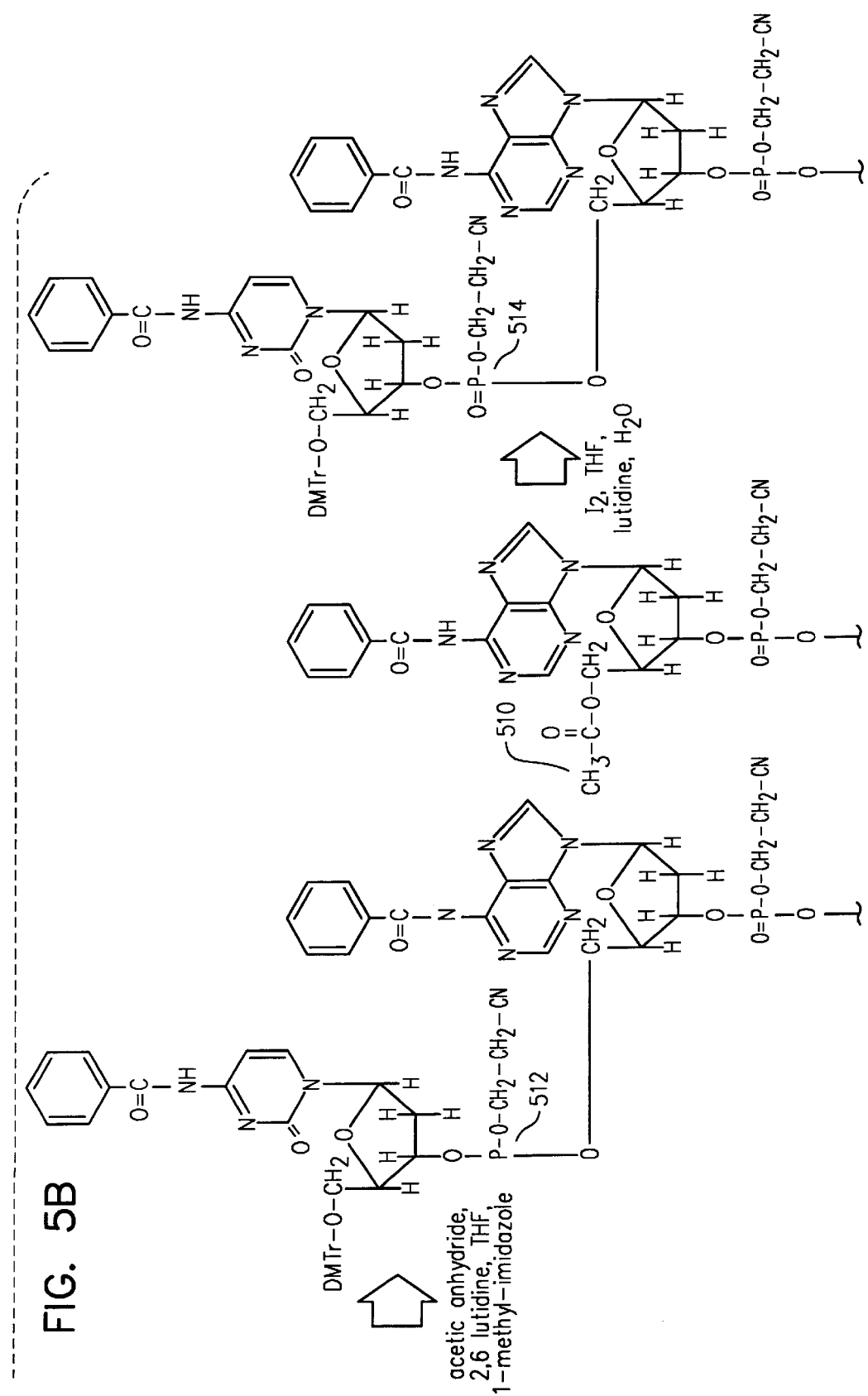

FIG. 8 shows the spreading, or blooming, of the regions containing appreciable concentrations of the unreacted protected deoxynucleoside phosphoramidites, applied to cells of an HDA in a synthetic step, during a subsequent washing step in which the unreacted deoxynucleoside phosphoramidites are removed from the surface of the HDA in a single bulk wash. As shown in FIG. 8, during the washing step, rather large, irregularly shaped regions 802–806 of the surface of the HDA are exposed to appreciable concentrations of unreacted deoxynucleoside phosphoramidites washed from the cells. For example, cells 808, 810, and 812 are exposed to appreciable concentrations of the protected deoxynucleoside phosphoramidite originally applied to cell 814. On certain substrates, unprotected functional groups of the substrate, or of molecules bound to the substrate, may react with the unreacted deoxynucleoside phosphoramidites and end up covalently bound to them. Thus, the deoxynucleoside phosphoramidites so precisely applied to the cells of the HDA in FIG. 7 end up, after the washing step, to be smeared into significantly lower resolution, irregularly shaped areas across the surface of the HDA, as shown in FIG. 8.

This spreading, or blooming, of applied phosphoramidite reagents may have a number of deleterious effects. First, because a given synthetic step may not proceed to 100% completion, a deoxynucleoside phosphoramidite applied to one cell may end up reacting with a growing oligonucleotide in a different cell that was either designated not to receive another nucleotide in the given synthetic step or was designated to receive a different nucleotide during the given synthetic step. Thus, the cells of the HDA will end up containing impure mixtures of a number of different oligonucleotides having potentially different lengths and potentially different nucleotide sequences. Also, when radioactive phosphoramidite markers or chemiluminescent phosphoramidite dyes are applied to cells of the HDA in order to mark particular cells or features for subsequent detection by radiometric or optical methods, the spreading, or blooming, of the radioactive markers or chemiluminescent dyes across the surface of the HDA may result in incorrect alignment and incorrect detection by the detection devices. Finally, unintended oligonucleotide or oligonucleotide derivatives may be deposited outside of the circular surface areas of the HDA cells. Impure substrate-bound oligonucleotide samples within cells or unintended oligonucleotides on regions of the surface of the HDA outside the cells may result in radio-labeled or chemiluminescent DNA or RNA molecules hybridizing to unintended and unexpected regions of the surface of the HDA. This will result in a general loss of signal to noise ratio during optical or radiometric analysis of the results of a hybridization experiment, and may even result in an incorrect analysis.

Figure 9:
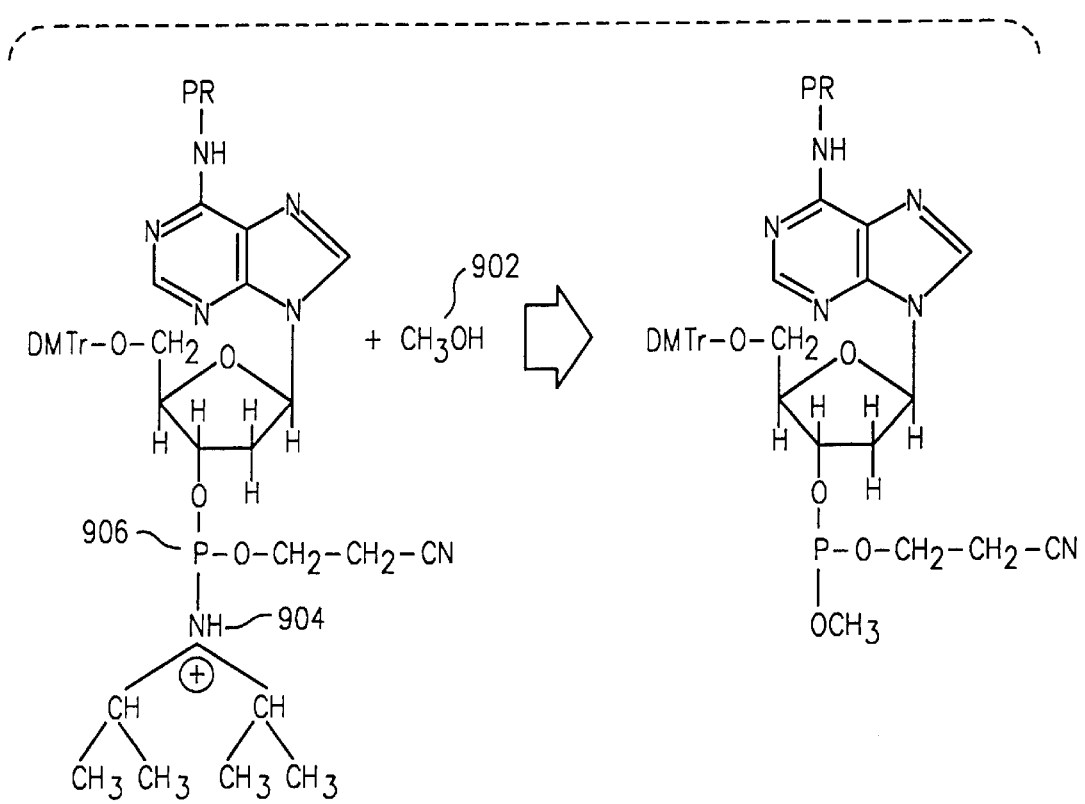
FIG. 9 shows the reaction of a protonated protected deoxynucleoside phosphoramidite with methanol to produce an unreactive protected deoxynucleoside phosphite triester.

FIG. 9 shows the reaction of a protonated protected deoxynucleoside phosphoramidite with methanol to produce the corresponding unreactive protected deoxynucleoside phosphite triester. The hydroxyl group of methanol 102 can displace the protonated secondary amine 904 of the phosphoramidite group 906 in the same way that the free hydroxyl groups of the chemically prepared substrate or 5' terminal end of a growing oligonucleotide displace the protenated secondary amine, as shown in FIGS. 4 and 5. Both protected deoxynucleoside phosphoramidites and tetrazole (or S-ethyl tetrazole or dicyanoimidazole) are soluble in methanol and methanol does not react with, or catalyze reactions of, either the growing oligonucleotide polymers or the substrate. Thus, in a preferred embodiment of the present invention, methanol is employed as a phosphoramidite-reactive wash reagent in place of the phosphoramidite-unreactive wash reagent acetonitrile in the wash steps of solid-state surface-bound oligonucleotide synthesis.

Figure 10A:
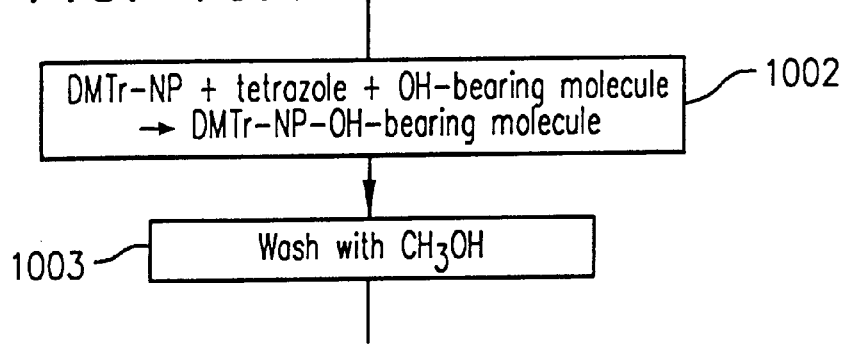
FIGS. 10A–10C illustrate three different modifications of solid-state oligonucleotide synthesis that prevent spreading, or blooming, of the reaction of phosphoramidite reactants during wash steps.
Figure 10B:
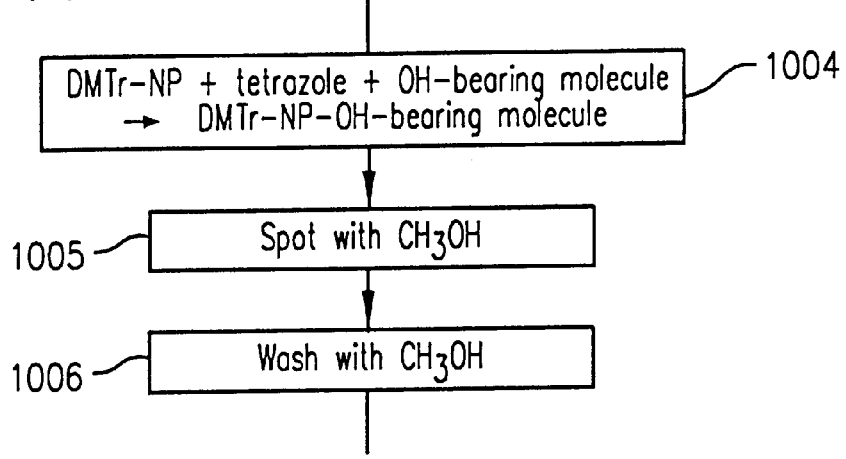
Figure 10C:
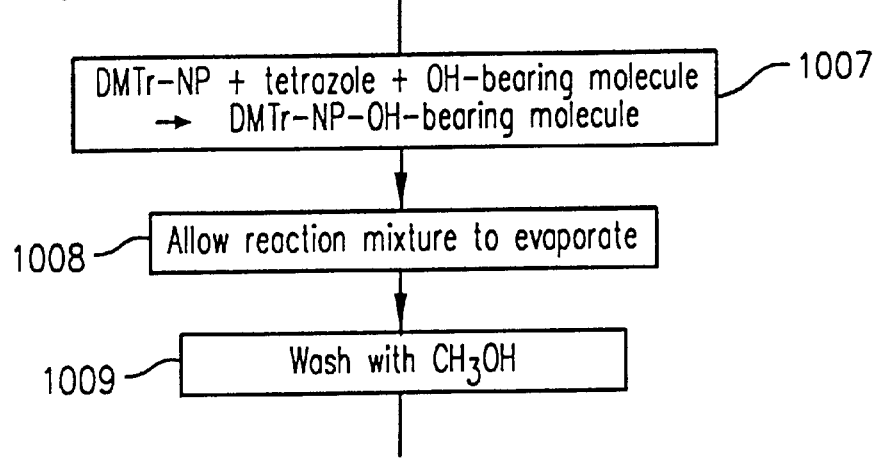

FIGS. 10A–10C illustrate three different modifications of solid-state oligonucleotide synthesis that prevent spreading, or blooming, of the protected deoxynucleoside phosphoramidite addition reaction during wash steps. Steps 1002–1003 of FIG. 10A, 1004–1006 of FIG. 10B, or 1007–1009 of FIG. 10C are substituted for steps 602 and 604 and for steps 618 and 620 of FIG. 6. Any single one of, or any combination of, the alternate embodiments represented by the steps of FIG. 10A–10C can be substituted for steps 602 and 604 and for steps 618 and 620 of FIG. 6 in order to produce a solid-state oligonucleotide synthetic procedure that eliminates the spreading, or blooming, of the reaction of phosphoramidite reagents with functional groups of, or bound to, the surface of HDA outside the region of the surface of the HDA to which the phosphoramidite reagents are applied.

In the first alternative embodiment shown in FIG. 10A, a protected deoxynucleoside phosphoramidite is applied, along with tetrazole, S-ethyl tetrazole, or dicyanoimidazole, in successive substeps to one or more designated cells of an HDA in step 1002. In step 1003, remaining unreacted protected deoxynucleoside phosphoramidites and tetrazole, S-ethyl tetrazole, or dicyanoimidazole are removed by bulk washing the surface of the HDA with methanol. In the embodiment represented in FIG. 10B, protected deoxynucleoside phosphoramidite and tetrazole, S-ethyl tetrazole, or dicyanoimidazole are applied, in successive substeps, to one or more designated cells of an HDA in step 1004. Then, in step 1005, methanol is applied to those designated cells in individual successive steps. Finally, in step 1006, the entire surface of the HDA is bulk washed with methanol to remove protected deoxynucleoside phosphite triesters, protonated secondary amines, and tetrazole, S-ethyl tetrazole, or dicyanoimidazole. In FIG. 10C, protected deoxynucleoside phosphoramidite and tetrazole, S-ethyl tetrazole, or dicyanoimidazole are applied, in successive sub-steps, to one or more designated cells within an HDA. In step 1008, the cells of the HDA are allowed to evaporate to dryness. In step 1009, the dry surface of the HDA is flooded and washed with methanol. By allowing the cells to evaporate, the methanol wash reagent applied in step 1009 will react with unreacted protected deoxynucleoside phosphoramidites as they enter into solution, prior to their displacement from the circular area of the substrate onto which the contents of the cell are deposited during the evaporation step. Analogous embodiments, using methanol as a wash reagent, may be applied to removing unreacted phosphoramidite dyes and markers that have been applied to the surface of an HDA in order to prevent spreading, or blooming, of the dyes or markers.

Although the present invention has been described in terms of a particular embodiment, it is not intended that the invention be limited to this embodiment. Modifications within the spirit of the invention will be apparent to those skilled in the art. For example, any number of different phosphoramidite-reactive wash agents may be devised. A large number of different types of solvents containing free hydroxyl or primary amine groups may be employed as phosphoramidite-reactive wash reagents. Moreover, a phosphoramidite-reactive wash agent may be produced by adding one or more phosphoramidite-reactive substances to an otherwise phosphoramidite-unreactive solvent. As another example, the present invention may be applied during the preparation of HDAs that contain biopolymers other than oligonucleotides. Wash reagents that react with, and quench, unreacted reactive monomers may be used to prevent blooming of the reaction of the unreacted monomers to areas of the HDA outside of the areas to which the reactive monomer is applied.

The foregoing description, for purposes of explanation, used specific nomenclature to provide a thorough understanding of the invention. However, it will be apparent to one skilled in the art that the specific details are not required in order to practice the invention. The foregoing descriptions of specific embodiments of the present invention are presented for purpose of illustration and description. They are not intended to be exhaustive or to limit the invention to the precise forms disclosed. Obviously many modifications and variations are possible in view of the above teachings. The embodiments are shown and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents.

What is claimed is:

1. A method used, during the solid-state synthesis of surface-bound polymers on a solid substrate, for removing a reaction solution including unreacted reactive reagents from the surface of the solid substrate and from any nascent polymers bound to the solid substrate, the method comprising:

selecting a reactive wash solution that is not reactive toward, and does not catalyze reactions with, the solid substrate or any nascent polymers bound to the solid substrate but that reacts with, and deactivates, the reactive reagents and that is miscible with the reaction solution; and applying the reactive wash solution to the surface of the solid substrate in order to react with, and deactivate, any unreacted reactive reagents and to remove the reaction solution from the surface of the solid substrate and from any nascent polymers bound to the substrate.

2. The method of claim 1 wherein the reaction solution includes reactive monomers and a catalyzing reagent that catalyzes the coupling of reactive monomers to the nascent polymers.

3. The method of claim 2 wherein the reactive monomers are deoxynucleoside phosphoramidites and the polymers are oligonucleotides.

4. The method of claim 3 wherein the solid substrate is a high-density array comprising cells in which different oligonucleotides are synthesized, the method further including:

applying the reactive wash solution separately to each cell of the high-density array in order to react with, and deactivate, any unreacted deoxynucleoside phosphoramidites s; and rinsing the surface of the solid substrate with the reactive wash solution to remove the deactivated unreacted deoxynucleoside phosphoramidites and catalyzing reagent from the surface of the solid substrate and from any nascent polymers bound to the substrate.

5. The method of claim 3 wherein the solid substrate is a high-density array comprising cells in which different oligonucleotides are synthesized, the method further including:

applying the reactive wash solution separately to each cell of the high-density array in order to react with, and deactivate, any unreacted deoxynucleoside phosphoramidites;

allowing the applied reactive wash solution and reaction solution to evaporate; and rinsing the surface of the solid substrate with the reactive wash solution to remove the deactivated deoxynucleoside phosphoramidites and catalyzing agent from the surface of the solid substrate and from any nascent polymers bound to the substrate.

6. The method of claim 3 wherein the reactive wash solution includes a chemical compound containing a hydroxyl functional group.

7. The method of claim 6 wherein the reactive wash solution is methanol.

8. The method of claim 1 wherein the reaction solution includes a reactive dye.

9. The method of claim 1 wherein the reaction solution includes a reactive radio-labeled marker.

10. A method for coupling a reactive monomer molecule to a nascent polymer bound to surface of a solid substrate, the method comprising:

applying monomer molecules and any reagents required to catalyze the coupling of the reactive monomer molecule with the nascent polymer to the surface of the solid substrate; and applying a reactive wash solution to the surface of the solid substrate to react with, and deactivate, any remaining reactive monomers on the surface of the solid substrate and to dissolve and remove the remaining deactivated monomers and any reagents required to catalyze the coupling of the reactive monomer molecule to the polymer from the surface of the solid substrate and from any synthesized polymers bound to the substrate.

11. The method of claim 10 wherein the reactive monomers are deoxynucleoside phosphoramidites and the polymers are oligonucleotides.

12. The method of claim 11 wherein the solid substrate is a high-density array comprising cells in which different oligonucleotides are synthesized, the method further including:

applying the reactive wash solution separately to each cell of the high-density array in order to react with, and deactivate, any unreacted deoxynucleoside phosphoramidite s; and rinsing the surface of the solid substrate with the reactive wash solution to remove the deactivated unreacted deoxynucleoside phosphoramidite s and catalyzing reagent from the surface of the solid substrate and from any nascent polymers bound to the substrate.

13. The method of claim 12 wherein the solid substrate is a high-density array comprising cells in which different oligonucleotides are synthesized, the method further including:

applying the reactive wash solution separately to each cell of the high-density array in order to react with, and deactivate, any unreacted deoxynucleoside phosphoramidite s;

allowing the applied reactive wash solution and solution to evaporate; and rinsing the surface of the solid substrate with the reactive wash solution to remove the deactivated deoxynucleoside phosphoramidite s and catalyzing agent from the surface of the solid substrate and from any nascent polymers bound to the substrate.

14. The method of claim 11 wherein the reactive wash solution includes a chemical compound containing a hydroxyl functional group.

15. The method of claim 14 wherein the reactive wash solution is methanol.

* * * * *